(12) United States Patent
Epple

(10) Patent No.: US 11,103,690 B2
(45) Date of Patent: Aug. 31, 2021

(54) CATHETER PUMP COMPRISING DRIVE UNIT AND CATHETER

(71) Applicant: CardioBridge GmbH, Hechingen (DE)

(72) Inventor: Klaus Epple, Rangendingen (DE)

(73) Assignee: CardioBridge GmbH, Hechingen (DE)

( * ) Notice: Subject to any disclaimer, the term of this patent is extended or adjusted under 35 U.S.C. 154(b) by 111 days.

(21) Appl. No.: 16/484,808

(22) PCT Filed: Feb. 8, 2018

(86) PCT No.: PCT/EP2018/053131
§ 371 (c)(1),
(2) Date: Aug. 8, 2019

(87) PCT Pub. No.: WO2018/146177
PCT Pub. Date: Aug. 16, 2018

(65) Prior Publication Data
US 2020/0000988 A1 Jan. 2, 2020

(30) Foreign Application Priority Data

Feb. 13, 2017 (DE) ...................... 10 2017 102 824.2

(51) Int. Cl.
| | | |
|---|---|---|
| *A61M 25/00* | (2006.01) | |
| *A61M 60/857* | (2021.01) | |
| *A61M 60/135* | (2021.01) | |
| *A61M 60/419* | (2021.01) | |
| *A61M 60/422* | (2021.01) | |
| *A61M 60/818* | (2021.01) | |
| *A61M 60/829* | (2021.01) | |

(52) U.S. Cl.
CPC ...... *A61M 60/857* (2021.01); *A61M 25/0021* (2013.01); *A61M 60/135* (2021.01);
(Continued)

(58) Field of Classification Search
CPC .............. A61M 60/857; A61M 60/135; A61M 60/419; A61M 60/422; A61M 60/818;
(Continued)

(56) References Cited

U.S. PATENT DOCUMENTS

2002/0029006 A1* 3/2002 Turturro ................. A61B 10/06
600/562
2006/0229645 A1* 10/2006 Bonnette .......... A61B 17/00234
606/159

(Continued)

FOREIGN PATENT DOCUMENTS

DE 20 2009 018 145 U1 6/2011
DE 10 2013 011042 A1 1/2014
(Continued)

*Primary Examiner* — Shirley X Jian
(74) *Attorney, Agent, or Firm* — Aslan Law, P.C.

(57) ABSTRACT

A catheter including a cage having a distal and proximal sleeves and filaments running between sleeves and an actuation portion comprises a base part that is movement-coupled with the inner catheter in the axial direction and an actuation part that can be moved relative to the base part in the axial direction and is guided in or on the base part, the outer catheter's proximal end having the actuation part and the outer catheter's distal end having the proximal sleeve are movement-coupled in the axial direction such that when moving the actuation part away from the base part, the proximal sleeve is moved toward the distal sleeve, the actuation part comprises an inlet for irrigation fluid to be transferred to bearing points of the conveying element, and the base part has an outlet for irrigation fluid coming from the bearing points.

20 Claims, 2 Drawing Sheets

(52) U.S. Cl.
CPC ........ *A61M 60/419* (2021.01); *A61M 60/422* (2021.01); *A61M 60/818* (2021.01); *A61M 60/829* (2021.01); *A61M 2025/0004* (2013.01)

(58) Field of Classification Search
CPC ............ A61M 60/829; A61M 25/0021; A61M 2025/0004; A61M 60/205; A61M 25/04; A61M 25/0097; A61M 25/0074
See application file for complete search history.

(56) References Cited

U.S. PATENT DOCUMENTS

| | | | | |
|---|---|---|---|---|
| 2009/0292276 | A1* | 11/2009 | Nash | A61B 17/320758 606/7 |
| 2010/0016832 | A1* | 1/2010 | Thai | A61M 25/007 604/508 |
| 2011/0034874 | A1 | 2/2011 | Reitan | |
| 2011/0282128 | A1* | 11/2011 | Reitan | A61M 60/205 600/16 |
| 2017/0014562 | A1* | 1/2017 | Liebing | F04D 29/046 |
| 2017/0035954 | A1* | 2/2017 | Muller | A61M 60/829 |

FOREIGN PATENT DOCUMENTS

| | | | |
|---|---|---|---|
| EP | 2 246 078 A1 | 11/2010 | |
| EP | 2 745 869 A1 | 6/2014 | |
| GB | 2505068 A | 2/2014 | |
| JP | 2008-178690 | 8/2008 | |
| JP | 2011-525385 | 9/2011 | |
| JP | 2014-097395 | 5/2014 | |
| JP | 2015-21403 | 12/2015 | |
| WO | WO-0117581 A2 * | 3/2001 | ............ A61M 1/102 |
| WO | WO 2015/187838 A1 | 12/2015 | |

* cited by examiner

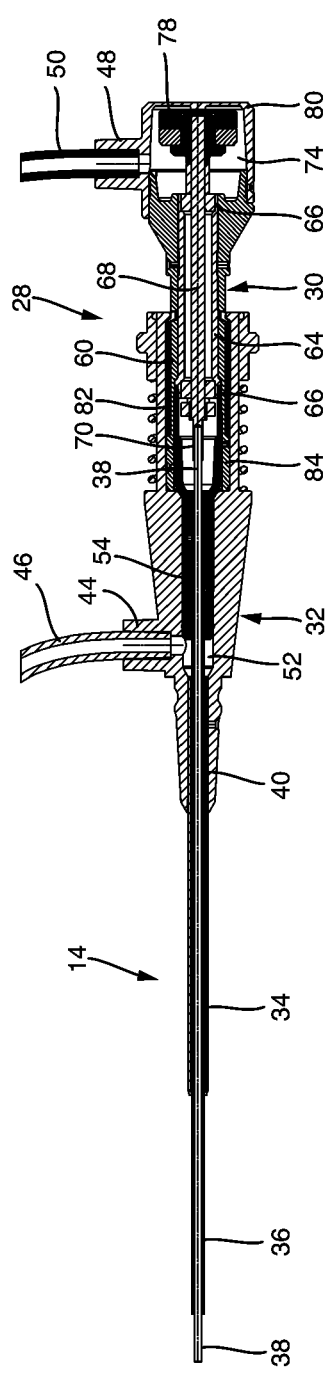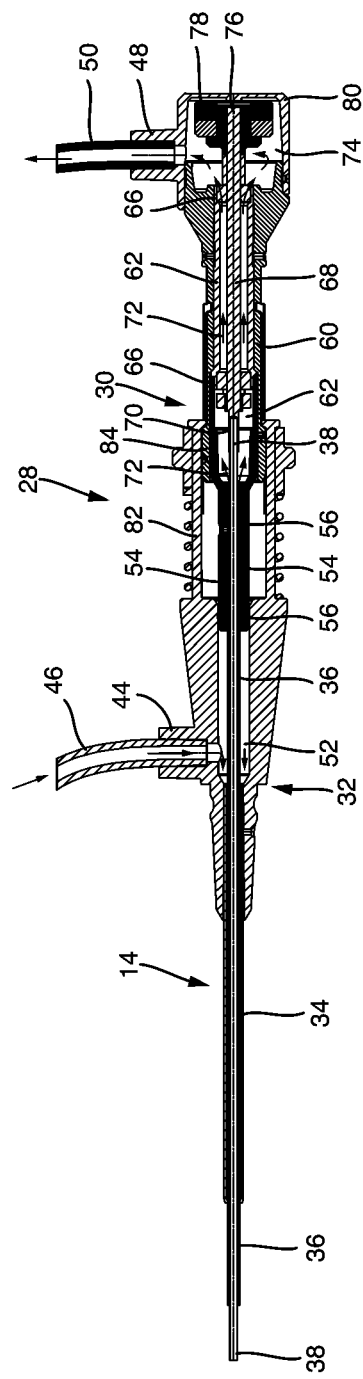

CATHETER PUMP COMPRISING DRIVE UNIT AND CATHETER

CROSS-REFERENCE TO RELATED APPLICATIONS

This application claims priority to German Patent Application No. 10 2017 102 824.2 filed on Feb. 13, 2017, and to PCT Application No. PCT/EP2018/053131 filed on Feb. 8, 2018, the entire contents of which are hereby incorporated by reference.

DESCRIPTION

Background of the Invention

Field of the Invention

The invention relates to a catheter pump having a catheter, having a pump head, provided at the distal end of the catheter, for introduction into the arterial vascular system, in particular into the aorta or heart, the catheter comprising an outer catheter and an inner catheter arranged in the outer catheter, having a rotor shaft, rotatably arranged in the inner catheter, for driving an expandable conveying element provided on the pump head, having an actuation portion, provided at the proximal end of the catheter, by means of which the rotor shaft can be driven, and having a cage surrounding the conveying element, the cage having a distal and a proximal sleeve and filaments running between the sleeves, it being possible for the proximal sleeve to be moved to expand the cage in the axial direction toward the distal sleeve. In the process, the regions of the filaments lying between the sleeves expand radially outward in order to form a chamber surrounding the expanding conveying element.

Description of the Related Art

Such catheter pumps are known, for example, from EP 2 288 392 A1 (US 2011/282128 A1). As described in EP 2 288 392 A1, for example, a rotor having propellers that can be unfolded can be used as a rotating conveying element, which rotor is provided at the distal end of the catheter. It is also conceivable that differently shaped conveying elements can be used, for example a helically formed spiral.

Catheter pumps are used as a temporary circulatory support system in the arterial vasculature, for example in the aorta of patients, in particular when the natural heart is unable to provide the body with sufficiently oxygenated blood. The conveying element and the rotor shaft are operated at relatively high speeds in the range of 7,000 to 15,000 revolutions. The pump head of the catheter pump may remain in the patient for several days.

The object of the present invention is that of providing a catheter pump of the type described at the outset, by means of which the cage can be expanded in a functionally reliable manner.

BRIEF SUMMARY OF THE INVENTION

This object is achieved by means of a catheter pump having the features of claim 1. According to the invention, the actuation portion thus has a base part that is movement-coupled with the inner catheter in the axial direction and an actuation part that can be moved relative to the base part in the axial direction and guided in or on the base part, the proximal end of the outer catheter being movement-coupled with the actuation part and the distal end of the outer catheter being movement-coupled with the proximal sleeve in the axial direction such that, when the actuation part moves away from the base part, the proximal sleeve is moved toward the distal sleeve.

Since the actuation part is arranged so as to be guided in or on the base part, a reliable relative movement can be ensured between the base part and actuation part. However, since the proximal end of the outer catheter is movement-coupled with the actuation part and the distal end of the outer catheter is movement-coupled with the proximal sleeve in the axial direction, actuating the actuation part relative to the base part means that the proximal sleeve is moved in the distal direction toward the distal sleeve, and so the filaments of the cage expand radially outward to provide a chamber surrounding a conveying element. The base part is preferably arranged so as to be proximal with respect to the actuation part, i.e. the actuation part is located between the base part and the pump head. When moving the actuation part toward the base part, it is preferable for not only the cage to expand, but also, at the same time or shortly thereafter, for the conveying element to be actuated from its collapsed or folded position into the expanded position.

For sufficient lubrication and irrigation of the bearing points of the conveying element, the actuation part has an inlet for irrigation fluid and the base part has an outlet for the irrigation fluid coming from the bearing points. In this respect, irrigation fluid can be pumped into the catheter and guided to the bearing points via the actuation part or the inlet thereof. At least some of the introduced irrigation fluid can be removed from the catheter via the base part or the outlet thereof.

It is advantageous if the actuation part has an inlet chamber connected to the inlet, the inner catheter extending through the inlet chamber and the inlet chamber being connected to an inlet lumen provided between the outer catheter and the inner catheter, and so irrigation fluid coming through the inlet can flow via the inlet chamber and the inlet lumen toward the bearing points of the conveying element. As a result, the irrigation fluid does not come into contact with the shaft rotating in the inner catheter. Contamination of the irrigation fluid can thus be prevented. The inner catheter, which has the rotor shaft rotating therein during operation, can nevertheless be guided safely through the inlet chamber to the base part.

In order to still allow a relative movement between the actuation part and the base part, it is advantageous if the inlet chamber on the proximal side is delimited by a piston portion of the base part, which piston portion can be axially displaced in the inlet chamber. This piston portion advantageously receives the proximal end of the inner catheter, through which the rotor shaft extends toward the proximal end of the base part. Providing the piston portion means that no irrigation fluid can flow in the proximal direction out of the actuation part; however, the actuation part can be moved relative to the base part in the axial direction. Preferably, the piston portion comprises on the radial outer side thereof a circumferential sealing ring, which both allows axial displacement and also ensures the tightness of the inlet chamber. The inlet chamber is advantageously of the smallest volume possible in order to change the volume of the inlet chamber as little as possible upon actuation of the actuation portion.

It is also advantageous if the base part comprises a sleeve-like bearing portion having a receiving chamber, in which bearing points are provided for rotationally mounting the proximal end of the rotor shaft. The base part thus provides on the distal portion thereof the piston portion and in the proximal direction the bearing portion attached thereto. The rotor shaft extends in the axial direction through the receiving chamber. The rotor shaft as such can be formed in one piece or in several pieces. In order to achieve effective mounting of the proximal end of the rotor shaft, it is advantageous if said shaft is rigid in the receiving chamber. In the catheter, however, the rotor shaft can be designed so as to be flexible, so that the catheter, together with the rotor shaft, has a certain amount of flexibility. A bearing sleeve may be provided in the receiving chamber, in which bearing sleeve bearing points in the form of rotary bearings, in particular in the form of sliding roller bearing rings, are fixed. Two mutually axially spaced bearing points are preferably provided to ensure secure mounting of the proximal end of the rotor shaft, in particular in the axial and radial direction. In order to remove the irrigation fluid and for lubricating the rotor shaft rotating in the inner catheter, it is advantageous if the receiving chamber is connected to an outlet lumen provided between the inner catheter and the rotor shaft, such that irrigation fluid coming through the outlet lumen can flow via the receiving chamber toward the outlet.

The arrangement is such that the irrigation fluid, which flows from the outlet lumen into the receiving chamber, flows through the bearing points by means of which the proximal end of the rotor shaft is mounted, for cooling, irrigation and lubrication. The rotational bearing may have cut-outs, for example in the form of holes extending in the axial direction, through which the irrigation fluid can be guided.

The base part also advantageously provides at the proximal end thereof an outlet chamber connected to the outlet, the irrigation fluid coming from the receiving chamber flowing away through the outlet chamber into the outlet, after it has advantageously flowed through the bearing points.

The proximal free end of the rotor shaft preferably provides a rotational coupling portion provided in the outlet chamber. The rotary coupling portion can be contactlessly rotatably coupled to a drive by means of magnetic elements.

Further, to secure mutual guidance of the actuation part and the base part, it is advantageous if the actuation part has at the proximal end thereof a cylindrical sliding receptacle for a piston-like sliding portion of the base part. As a result, secure axial actuation of the actuation part and the base part can be achieved without the parts being able to be bent when moving toward one another.

The sliding portion is advantageously formed in portions by the outside of the bearing portion.

DETAILED DESCRIPTION OF THE INVENTION

Further advantages and advantageous embodiments of the invention can be found in the following description, on the basis of which an embodiment of the invention is described and explained in more detail.

In the drawings:

FIG. 2 is a longitudinal section through the actuation portion of the catheter pump according to FIG. 1 in a non-actuated introduction position of the pump head; and FIG. 3 shows the actuation portion according to FIG. 1 in the actuated operating position.

Figure 1:
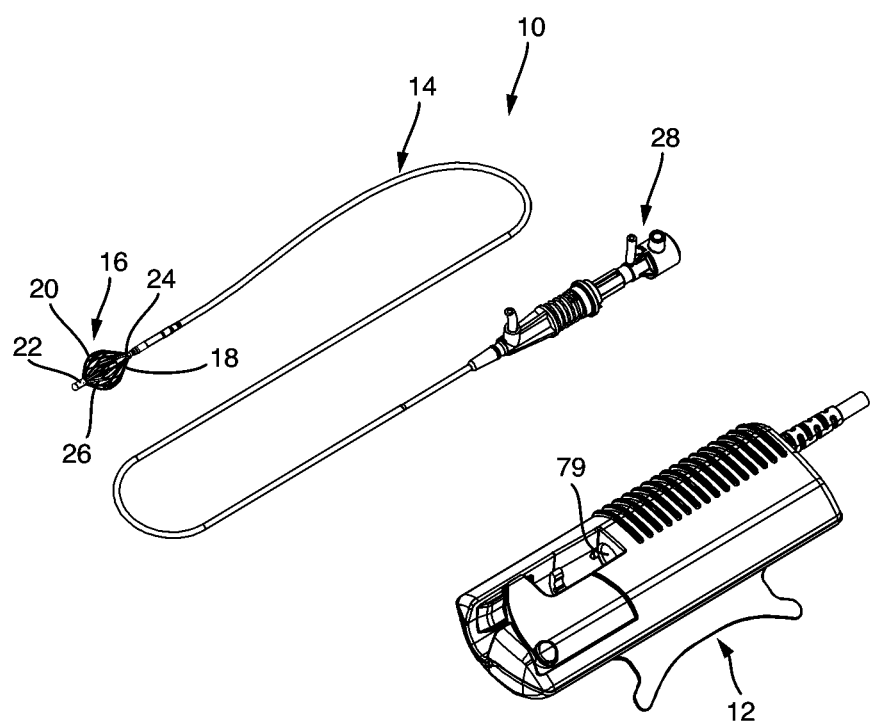
FIG. 1 shows a catheter pump comprising a drive unit and a catheter.

FIG. 1 shows a catheter pump 10 and a drive unit 12 for driving the catheter pump 10. The catheter pump 10 has a catheter 14 and, at the distal end, a pump head 16 for introduction into in particular the aorta or the heart. A rotor shaft is provided in the catheter 14, by means of which a conveying element 18, for example a rotor with propellers that can be unfolded, provided in the pump head 16 can be set in rotation. The conveying element 18 is surrounded by a cage 20 which has a distal sleeve 22 and a proximal sleeve 24 and filaments 26 running between the sleeves. To expand the cage 20 and also the conveying element 18, the proximal sleeve 24 is moved in the axial direction toward the distal sleeve 22.

At its proximal end, the catheter 14 provides an actuation portion 28, by means of which the proximal sleeve 24 can be moved toward the distal sleeve 22. Furthermore, the actuation portion 28 can be inserted into the drive unit 12, by means of which the rotor shaft, and thus the conveying element 18, can finally be set in rotation.

In the sections according to FIGS. 2 and 3, the actuation portion 28 is shown which comprises a base part 30 and an actuation part 32 which can be moved relative to the base part 30 in the axial direction. As is also clear, the catheter 14 has an outer catheter 34 and an inner catheter 36 which is axially displaceable in the outer catheter 34. The rotatable rotor shaft 38 is provided in the inner catheter 36.

In order to unfold the cage 20 or the conveying element 18, the actuation part 32 is thus moved away from the base part 30 in the distal direction, starting from the basic state shown in FIG. 2, until it finally assumes the actuation state shown in FIG. 3, in which the cage 20, or the filaments 26 thereof, is/are unfolded. In this actuation state, the actuation portion 28 is located in the drive unit 12 shown in FIG. 1. The rotor shaft can then be driven so as to drive the conveying element 18 by means of a drive motor provided therein, as described below.

The outer catheter 34 is arranged by means of its proximal end 40 so as to be fixed on the actuation part 32. The inner catheter 36 engages in the actuation part 32 in the axial direction and is arranged by means of its proximal end 58 so as to be fixed to the base part 30.

By axially actuating the actuation part 32 relative to the base part 30, the outer catheter 34 can thus be moved relative to the inner catheter 36. Since the distal sleeve 22 of the cage 20 is movement-coupled with the inner catheter 36 and the proximal sleeve 24 is movement-coupled with the outer catheter in the axial direction, a relative movement of the actuation part 32 relative to the base part 30, and thus of the outer catheter 34 with respect to the inner catheter 36, can move the proximal sleeve 24 toward the distal sleeve 22 or away from the distal sleeve 22 in order to expand the cage 20 or to collapse or fold the cage 20. The movement-coupling is such that not only the cage 20 but also the conveying element 18 is expanded in the distal direction, either simultaneously together with the cage 20 or preferably shortly thereafter, when the actuation part 32 is moved.

As is clear from FIGS. 1 and 2, the actuation part 32 has an inlet 44 in which a hose 46 is located, via which irrigation fluid can be pumped to the bearing points of the conveying element 18. Correspondingly, there is an outlet 48 in the base part 30, in which outlet there is a hose 50, via which irrigation fluid coming from the bearing points of the conveying element 18 can be removed.

During operation, irrigation fluid, as shown in FIG. 3, thus flows via the hose 46 into the inlet 44. An inlet chamber 52 connected to the inlet 44 is provided in the actuation part 32 and is connected to an inlet lumen provided between the outer catheter 34 and the inner catheter 36. As a result, irrigation fluid can flow from the inlet chamber 52 via the inlet lumen to the bearing points of the conveying element 18 at the distal end of the catheter 14.

As is clear from FIGS. 2 and 3, the inlet chamber 52 is delimited on the proximal side by a piston portion 54 of the base part 30 which is axially displaceable in the inlet chamber 52 and dips into the inlet chamber 52. In order to allow sufficient sealing between the free end of the piston portion 54 and the wall of the inlet chamber 52, a sealing ring 56 is provided on the piston portion 54 in a circumferential groove.

The piston portion 54 also receives the proximal end 58 of the inner catheter 36. As a result, the proximal end 58 of the inner catheter 36 is connected in the axial direction so as to be movement-coupled with the piston portion 54.

The base part 30 also has a sleeve-like bearing portion 60 which forms a receiving chamber 62. In the receiving chamber 62, a bearing sleeve 64 is accommodated, in which two axially spaced rotary bearings 66 are provided, which rotationally mount the proximal end portion 68 of the rotor shaft 38. The rotor shaft 38, or the end portion 68 thereof, extends through the receiving chamber 62. The end portion 68 of the rotor shaft 38 is formed as a rigid shaft which is connected by means of a coupling portion 70 to the flexible part of the rotor shaft 38.

The receiving chamber 62 is also connected to an outlet lumen provided between the inner catheter 36 and the rotor shaft 38. At its proximal end, the base part 30 has an outlet chamber 74 which is connected to the outlet 48 and is connected to the outlet 48 or the hose 50. Therefore, the irrigation fluid coming from the bearing points of the conveying element 18 can flow, via the outlet lumen, the receiving chamber 62 and the outlet chamber 74, to the outlet 48 or hose 50, as indicated by arrow lines 72. As a result, on the one hand the rotor shaft 38, which rotates during operation in the inner catheter 36, is lubricated and on the other hand the rotary bearings 66 can be sufficiently lubricated and cooled.

A rotary coupling portion 78 is provided at the free, proximal end 76 of the rotor shaft 38, or at the end portion 68 thereof. The rotary coupling portion 78 comprises a magnetic ring, which can be set in rotation by means of magnetic coupling by a drive-side magnet ring 79 indicated in FIG. 1. On the rotor shaft 38, or on the end portion 68 thereof, a further magnet may be provided, by means of which it is possible to detect whether the shaft is rotating or not, or at what speed it is rotating, by means of a corresponding sensor in the drive unit.

As is also clear from FIGS. 2 and 3, the base part 30 has at its proximal end a cap 80 which covers the outlet chamber 74 and which also contains the outlet 48.

For secure guidance of the actuation part 32 relative to the base part 30, a cylindrical sliding receptacle 82 is provided at the proximal end of the actuation part 32. A piston-like sliding portion 84 of the base part 30 is displaceably accommodated in the sliding receptacle 82. The sliding portion 84 is formed by portions of the lateral surface of the bearing portion 60. By providing the sliding portion 84 and the associated sliding receptacle 82, a secure axial movement of the actuation part 32 on the base part 30 can be made possible.

The base part 30 and the actuation part 32 may be formed integrally or in several pieces. In the embodiment shown in the drawing, the base part 30 consists of several individual parts, such as the piston portion 54, the bearing portion 60, together with the bearing sleeve 64 and the cap 80.

The invention claimed is:

1. A Catheter pump having a catheter, the Catheter pump having a pump head provided at the distal end of the catheter for introduction into the arterial vascular system, the catheter comprising:
   an outer catheter;
   an inner catheter arranged in the outer catheter;
   a rotor shaft rotatably arranged in the inner catheter for driving an expandable conveying element provided on the pump head;
   an actuation portion provided at the proximal end of the catheter, by means of which the rotor shaft can be driven, and
   a cage surrounding the conveying element, wherein
   the cage having a distal and a proximal sleeve and filaments running between the distal and the proximal sleeve, wherein the proximal sleeve is movable in the axial direction toward the distal sleeve to expand the cage,
   the actuation portion comprises a base part that is movement-coupled with the inner catheter in the axial direction and an actuation part that can be moved relative to the base part in the axial direction and is guided in or on the base part,
   the proximal end of the outer catheter having the actuation part and the distal end of the outer catheter having the proximal sleeve are movement-coupled in the axial direction such that when moving the actuation part away from the base part, the proximal sleeve is moved toward the distal sleeve,
   the actuation part comprises an inlet for irrigation fluid to be transferred to bearing points of the conveying element, and
   the base part has an outlet for irrigation fluid coning from the bearing points.

2. The Catheter pump according to claim 1, wherein
   the actuation part comprises an inlet chamber connected to the inlet,
   the inner catheter extending through the inlet chamber, and
   the inlet chamber being connected to an inlet lumen provided between the outer catheter and the inner catheter such that irrigation fluid coming through the inlet can flow via the inlet chamber and the inlet lumen to the bearing points of the conveying element.

3. The Catheter pump according to claim 2, wherein
   the inlet chamber on the proximal side is delimited by a piston portion of the base part that is axially displaceable in the inlet chamber, on which base part the proximal end the inner catheter is fastened and through which the rotor shaft extends.

4. The Catheter pump according to claim 2, wherein the base part comprises a sleeve-like bearing portion having a receiving chamber, in which bearing points are provided for rotationally mounting the proximal end of the rotor shaft.

5. The Catheter pump according to claim 2, wherein
   the proximal, free end of the rotor shaft has a rotary coupling portion.

6. The Catheter pump according to claim 3, wherein
   the base part comprises a sleeve-like bearing portion having a receiving chamber, in which bearing points are provided for rotationally mounting the proximal end of the rotor shaft.

7. The Catheter pump according to claim 3, wherein
   the proximal, free end of the rotor shaft has a rotary coupling portion.

8. The Catheter pump according to claim 1, wherein
the base part comprises a sleeve-like bearing portion having a receiving chamber, in which bearing points are provided for rotationally mounting the proximal end of the rotor shaft.

9. The Catheter pump according to claim 8, wherein
a bearing sleeve is provided in the receiving chamber, in which the bearing points in the form of rotary bearings are fixed.

10. The Catheter pump according to claim 8, wherein
the proximal, free end of the rotor shaft has a rotary coupling portion.

11. The Catheter pump according to claim 9, wherein
the rotary bearings comprise cut-outs, through which the irrigation fluid can be guided.

12. The Catheter pump according to claim 9, wherein
the receiving chamber is connected to an outlet lumen provided between the inner catheter and the rotor shaft such that irrigation fluid coming through the outlet lumen can flow via the receiving chamber to the outlet.

13. The Catheter pump according to claim 9, wherein
the proximal, free end of the rotor shaft has a rotary coupling portion.

14. The Catheter pump according to claim 11, wherein
the receiving chamber is connected to an outlet lumen provided between the inner catheter and the rotor shaft such that irrigation fluid coning through the outlet lumen can flow via the receiving chamber to the outlet.

15. The Catheter pump according to claim 11, wherein
the proximal, free end of the rotor shaft has a rotary coupling portion.

16. The Catheter pump according to claim 12, wherein
the proximal, free end of the rotor shaft has a rotary coupling portion.

17. The Catheter pump according to claim 1, wherein the base part has at its proximal end an outlet chamber connected to the outlet, the irrigation fluid coming from a receiving chamber flows out, through the outlet chamber, into the outlet.

18. The Catheter pump according to claim 1, wherein
the proximal, free end of the rotor shaft has a rotary coupling portion.

19. The Catheter pump according to claim 1, wherein
the actuation part has at its proximal end, a cylindrical sliding receptacle for a piston-like sliding portion of the base part.

20. The Catheter pump according to claim 19, wherein the sliding portion is formed, at least in portions, by a sleeve-like bearing portion of the base part.

\* \* \* \* \*